(12) United States Patent
Montasser

(10) Patent No.: US 8,138,390 B2
(45) Date of Patent: Mar. 20, 2012

(54) BIOLOGICAL CONTROL AGENT FOR PLANTS

(75) Inventor: Magdy S. Montasser, Safat (KW)

(73) Assignee: Kuwait University, Safat (KW)

( * ) Notice: Subject to any disclaimer, the term of this patent is extended or adjusted under 35 U.S.C. 154(b) by 127 days.

(21) Appl. No.: 12/662,852

(22) Filed: May 6, 2010

(65) Prior Publication Data

US 2011/0274659 A1    Nov. 10, 2011

(51) Int. Cl.
*C12N 7/00* (2006.01)
*C12N 7/02* (2006.01)
*C12N 7/04* (2006.01)
*C12N 15/83* (2006.01)

(52) U.S. Cl. ..... 800/280; 800/279; 435/239; 435/235.1; 536/23.72

(58) Field of Classification Search .................. 800/280
See application file for complete search history.

(56) References Cited

OTHER PUBLICATIONS

Montasser et al. Satleelite-mediated protection of tomato against cucumber mosaic virus: I. Greenhouse experiments and simulated epidemic conditions in the field (1991a) Plant Disease 75: 86-92.*
Qin et al. Plant resistance to fungal diseases induced by the infection of cucumber mosaic virus attenuated by satellite RNA (1992) Annals App. Biol. 120: 361-366.*
Montasser et al. First report of potential biological conteol of potato spindle tuber viroid disease by virus-satellite combination (1991b) Plant Disease 75: 319.*

* cited by examiner

*Primary Examiner* — Russell Kallis
*Assistant Examiner* — Steven Bernacki
(74) *Attorney, Agent, or Firm* — Richard C. Litman

(57) ABSTRACT

A biological control agent for plants and a method of inoculating the plants with the biological control agent in order protect against plant disease are provided. The treatment method consists of inoculating the plant with a strain of cucumber mosaic virus (CMV), referred to as the KU1 strain, having an associated viral satellite RNA of SEQ ID NO: 1. Particularly, the KU1 strain may be used to protect plants against a particular viral strain of CMV, referred to as the KU2 strain, characterized by the associated viral satellite RNA of SEQ ID NO: 2, which causes tomato necrosis. Additionally, the KU1 strain may be used to protect against potato spindle tuber viroid (PSTV), which causes tomato stunting, *fusarium* wilt disease in the tomato (caused by *Fusarium oxysporum* f. sp. *Lycopersicae*), and leaf spotting disease in the tomato (caused by *Alternaria alternate*).

9 Claims, No Drawings

SEQUENCE LISTING

<160> NUMBER OF SEQ ID NOS: 2

<210> SEQ ID NO 1
<211> LENGTH: 345
<212> TYPE: RNA
<213> ORGANISM: cucumber mosaic virus

<400> SEQUENCE: 1

| aucuauagug | gauagugaaa | ugcguauggu | gauugaaucg | acguaaugau | cuaucacugg | 60 |
| ccggugugac | uaaccucacu | gcuuggccga | guugagcuga | gcagccuccg | ucagcggacu | 120 |
| gcuggcaugc | gugccauguc | cgcuacacuc | agcaccacgc | acucauuuga | gcuaacgcuc | 180 |
| aguaugcuag | cauuaccggg | ccugacgaug | gaagucagcg | cguuaaaucg | acgaguuaca | 240 |
| gcucagaaag | caagcuggca | gcguugaucg | ggucaaucgu | cuagcaauua | gcgaagcaag | 300 |
| ucuugccgau | cuccgugaau | gacuaacaau | ggauuacagc | uagca |  | 345 |

<210> SEQ ID NO 2
<211> LENGTH: 415
<212> TYPE: RNA
<213> ORGANISM: Cucumber necrosis virus

<400> SEQUENCE: 2

| aaguugcauu | gauuggagaa | augccgcagc | aggcgguuau | uaucucggug | aucugucacu | 60 |
| ccggcggugg | gaaaccuccc | ugcaaggcgg | uugaagugaa | aggccucgga | gggaccgcug | 120 |
| ggaucuguca | cucggcggug | ugggauaccu | cccugcuaag | gcgggUugag | ugauguuccc | 180 |
| ucggacuggg | accgcuggcu | ugcgagcuau | gucccuacuc | ucaguacuac | acucucauuu | 240 |
| gagcccgcgc | gcucaguuug | cuagcagaac | ccggcacaug | guucgccgau | acuauggauu | 300 |
| ucuaaagaaa | cacucuguua | gguguauug | aguuaugacg | acgcagggag | aggcuaaggc | 360 |
| uuaugcuaug | cugaaucucu | ccgugaaugu | cuauggaauc | cucgcaggau | uccgg | 415 |

BIOLOGICAL CONTROL AGENT FOR PLANTS

BACKGROUND OF THE INVENTION

1. Field of the Invention

The present invention relates to the prevention of diseases in plants, and particularly to a biological control agent for plants that provides for inoculating a plant with a satellite ribonucleic acid (RNA) associated with cucumber mosaic virus.

2. Description of the Related Art

Cucumber mosaic virus (CMV) is a plant pathogenic virus in the family Bromoviridae. It is the type member of the plant virus genus *Cucumovirus*. This virus has a worldwide distribution and a very wide host range. In fact, CMV has the reputation of having the widest host range of any known plant virus (191 hosts in 40 families). CMV can be transmitted from plant to plant, both mechanically by sap and also by aphids in a stylet-borne fashion. CMV can also be transmitted in seeds and by the parasitic weeds *Cuscuta* sp.

The cucumber mosaic virus was first found in cucumbers (*Cucumis sativus*) showing mosaic symptoms in 1934; hence, the name "Cucumber mosaic". Since it was first recognized, it has been found to infect a great variety of other plants. These include other vegetables, such as squash, melons, peppers, beans, tomatoes, carrots, celery, lettuce, spinach and beets, along with various weeds, and many ornamentals and bedding plants. Symptoms seen with this virus include leaf mosaic or mottling, yellowing, ringspots, stunting, and leaf, flower and fruit distortion.

CMV is a linear, positive-sense, single-stranded RNA virus. The virus contains three genomal RNAs of approximately 4,000 residues, 3,400 residues, and 2,200 residues, respectively, and a subgenomic RNA encoding the viral coat.

The cucumber mosaic virus is often found to be accompanied by small RNA molecules referred to as satellite RNA, which are not self-replicating, but depend upon association with CMV for replication, encapsidation, and transmission. Thus, satellite RNA exhibits the characteristics of a molecular parasite. Many strains of satellite RNA have the effect of reducing or attenuating the harmful or damaging effects of CMV on the host plant, while a few strains of satellite RNA either have the effect of accentuating the harmful or damaging effects of CMV, or result in no noticeable or significant attentuation of the virus.

Presently, no chemicals can cure a plant of this virus infection, or of any other viral infection. Control measures for all plant viruses presently include only prevention and eradication.

Plants are also subject to diseases from exposure to viroids (short molecules of circular, single-stranded RNA without a protein coat, such as the potato spindle tuber viroid) and from exposure to fungi, such as *Fusarium oxysporum* f. sp. *Lycopersicae* and *Alternaria alternate*. A natural treatment alternative to chemical sprays would be desirable due to environmental concerns about chemical treatment. Thus, a biological control agent for plants solving the aforementioned problems is desired.

SUMMARY OF THE INVENTION

The biological control agent for plants provides for inoculating plants with the biological control agent in order protect the plants from various forms of plant disease. The method consists of inoculating a healthy plant with a satellite RNA associated with cucumber mosaic virus. The satellite RNA has the sequence of nucleotides shown in SEQ ID NO: 1 in the attached Sequence Listing.

This strain of CMV with the associated satellite RNA (hereinafter referred to as the KU1 strain of CMV) has been found effective against a CMV strain referred to as the KU2 strain having a particular satellite RNA identified in SEQ ID NO: 2 associated therewith, the KU2 strain of CMV causing tomato necrosis. Additionally, the CMV strain having the satellite. RNA in SEQ ID NO: 1 may be used to treat and prevent potato spindle tuber viroid (PSTV), which causes tomato stunting, and to protect against *fusarium* wilt disease in the tomato (caused by *Fusarium oxysporum* f. sp. *Lycopersicae*) and leaf spotting disease in the tomato (caused by *Alternaria alternate*).

These and other features of the present invention will become readily apparent upon further review of the following specification.

DETAILED DESCRIPTION OF THE PREFERRED EMBODIMENTS

The biological control agent for plants relates to the use of a satellite RNA associated with cucumber mosaic virus (CMV) as a biological control agent against a CMV strain that causes tomato necrosis. Particularly, a strain of CMV, herein referred to as the KU1 strain, is used as a biological control agent against a particular viral strain that causes tomato necrosis, herein referred to as the KU2 strain. Additionally, the KU1 strain has been found effective in treating, and may be used to treat and prevent, potato spindle tuber viroid (PSTV), which causes tomato stunting, *fusarium* wilt disease in the tomato (caused by *Fusarium oxysporum* f. sp. *Lycopersicae*), and leaf spotting disease in the tomato (caused by *Alternaria alternate*).

The KU1 strain of CMV has been found to include the satellite RNA having the sequence identified as SEQ ID NO: 1.

The KU2 strain of CMV has been found to include the satellite RNA having the sequence identified as SEQ ID NO: 2.

The naturally occurring satellite RNA parasite of SEQ ID NO: 1 in the viral genome of the KU1 strain was discovered at the molecular level. This viral parasite was first characterized, and then used as a biological control agent to protect tomato plants against not only the disease induced by severe CMV strains, such as the KU2 strain, but also against potato spindle tuber viroids (PSTV) and fungal diseases caused by *Fusarium* sp. and *Alternaria* sp. in tomato plants. In plant growth chambers, tomato plants were pre-inoculated or "vaccinated" with the KU1 strain and then inoculated with a severe strain, such as KU2 and those described above, at varying time intervals. All plants tested three weeks after pre-inoculation with KU1 showed nearly complete protection from subsequent infection by the severe strains.

Two separate strains of cucumber mosaic virus (CMV) isolated in Kuwait have proven to be infective (based on symptomatology and host range) on different cultivars of tomato (*Lycopersicon esculent*), tobacco (*Nicotiana tabacum* L.) and squash (*Cucurbita pep*). The patterns of symptom appearance differed for the two strains in tomatoes and tobacco, showing severe symptoms with one strain (designated as "KU2") and almost symptomless with the other strain (the KU1 strain of the virus). White Bush F1 hybrid cultivar of squash, which was found highly susceptible to both viral strains in comparison to other cultivars, rapidly and visibly showed local symptoms, along with known systemic symptoms. Viability and infectivity of these strains in extracted nucleic acid inoculums was further proved by mechanical transmission.

Increased nucleic acid yields as double-stranded DNA, RNA and single-stranded RNA were also found in virus-infected plants, compared to healthy plants with a lower yield. As noted above, a naturally occurring satellite RNA parasite was found at the molecular level in the viral genome of the KU1 strain. This viral parasite, given by the above sequence listing (SEQ ID NO: 1) for the KU1 strain, is used as a biological control agent to protect tomato plants against not only the diseases induced by severe CMV strains, but also against potato spindle tuber viroids (PSTV), and fungal diseases caused by *Fusarium oxysporum* f. sp. *Lycopersicae* and *Alternaria alternata* in tomatoes.

The symptomatology was experimentally tested by inoculating both KU1 and two CMV strains on test plants by mechanical sap transmission. Inocula were prepared by grinding CMV-infected tissues (1 g/9 ml) in a 0.01 M potassium phosphate buffer (pH 7.1). The leaves of the young test plants were dusted with 600-mesh carborundum and then ground CMV-infected tissues were rubbed over those leaves with a cotton swab. Immediately after inoculation, sterilized distilled water was sprayed on the leaves. CMV infected tissues were rubbed on the cotyledonary leaves of 8-10 days old tomato (*Lycopersicon esculentum*), 5 to 7 days old squash (*Cucurbita pepo*) and 4 to 6 days old cowpea (*Vigna unguiculata*). Tobacco (*Nicotiana tabacum* L.) and Chenopodium (*Chenopodium morale*) were also inoculated at young stages.

Virus inoculated plants were kept in growth chambers (at 20, 22, and 24° C. for eight hours each and 16 hrs/8 hrs, light/dark periods) in 5.0 inch diameter pots containing a mixture of soil and peat potting substratum (1:2 V/V) provided with a complete fertilizer mix. Symptoms on test plants were observed until 30 days after inoculation. Once symptoms appeared on the test plants, the respective test plants were back-inoculated as CMV inocula for virus transmission in other test plants.

Additionally, total nucleic acids (TNAs) were extracted by powdering 0.25 g of infected tissue in liquid nitrogen in a sterile pre-cooled mortar and pestle. Fine powdered tissues were transferred to a 50 ml conical centrifuge tube with the help of a sterile brush. To this, 3 ml each of 1× extraction buffer (0.1 M glycine, 0.01 M EDTA, 0.1 M NaCl, pH 9.0 with 10% Sodium dodecyl sulfate (SDS) and 10% n-lauryl sarcocine), water saturated phenol (saturated with 10 mM Tris HCl and 1 mM EDTA) and chloroform were added. The homogenate was vortexed vigorously for 45 seconds and was centrifuged for 10 minutes at 5000 rpm at 4° C., and then kept on ice. The nucleic acids present in the upper aqueous layer were precipitated by adding three volumes of 95% ethanol in a 10 ml polypropylene copolymer tube and kept at −70° C. for 20 minutes. The precipitate was collected by centrifugation at 6500 rpm for 20 minutes. The pellet obtained was dissolved in 200 µl of 1× extraction buffer and shifted to 1.5 ml eppendorf tube followed by precipitation with three volumes of 95% ethanol at −70° C. for 15 to 20 minutes and then microcentrifugation at 10,000 rpm for 10 minutes.

The pellet obtained after decanting was dried and then dissolved in 200 µl of sterile distilled water. This total nucleic acid suspension was stored in a freezer at −70° C. TNAs extracted from virus infected plant tissues were further inoculated on test plants to check the viability of CMV viral strains as TNA inoculums. Extracted nucleic acid preparations were directly applied with glove-covered finger on plant leaves dusted with 600-mesh carborundum. Sterile distilled water was sprayed after TNA inoculum application.

Tomato plants showed severe infections when inoculated with TNA inoculums of KU2 infected tissues, but were symptomless in the inoculation with TNA from KU1 infected plants. Chlorotic spots and local chlorotic lesions were observed on squash cv. White Bush F1 hybrid inoculated with TNAs from either KU1 or KU2-infected plants.

Gel electrophoretic analyses showed average molecular weights of 3.3 kb and 1.0 kb for KU1 and KU2 infected squash TNA extracts, respectively, by analyzing a 6% gel at 200 V, while no band at that distance in the healthy specimens were observed. Nucleic acid bands of 374 bp and 400 by appeared in KU1-infected plants. Similarly, KU1, KU1 infected with KU2 extracts, and KU2 alone infected tomato extracts showed a 3.5 kb band when they analyzed on a 6% gel at 300 V. Additionally, extra bands of 292 bp and 330 bp in KU1 and KU1 infected with KU2 extracts were found, but these bands were missing in healthy and KU2-infected extracts.

For the gel electrophoreses of TNAs, polyacrylamide gel electrophoresis (PAGE) was used for the detection of satellite RNA and the other viral RNA molecules. TNA extracts were heated in a 50° C. water bath for five minutes, followed by quick cooling in crushed ice, then analyzed by electrophoresis on 6% polyacrylamide gels (39:1 acrylamide:bis acrylamide) in Tris borate EDTA (TBE) buffer, at 200V for 2.5 hr and 300V for 2 hr. The gel was stained with ethidium bromide and exposed to ultraviolet light for photographing.

CMV is a virus with a wide host range, differing in symptom appearance pattern according to the viral strain used. Test plants selected for experiment were susceptible to viral infection by both strains of CMV, namely KU1 and KU2. Results showed that the strains differed from one other, both in appearance of symptoms on different hosts and depending upon what were considered as mild strain KU1 and severe strain KU2 of CMV. The severe KU2 strain showed stunting, chlorosis and mosaic symptoms on tomatoes, and severe mosaics on squash, as well as on tobacco leaves. However, the KU1 strain was found as a mild strain, showing mosaic on squash leaves but being symptomless on tomatoes. Similarly, in tobacco plants, this KU1 strain showed mild mosaics on very young leaves, but later, the plants were found to be symptomless.

The study also found the appearance of local chlorotic spots on the cotyledon leaves of cultivar White Bush F1 hybrid squash along with the systemic symptoms on the rest of plant leaves. These local symptoms were more severe in plants inoculated with the KU2 strain. Extracted CMV nucleic acid was also viable and effective in inoculation tests. This was proved by back inoculating the test plants with extracted nucleic acids of virus-infected plants.

Preliminary level pre-inoculation and challenge inoculation showed a complete protection in plants tested three weeks after pre-inoculation, followed by two weeks, with the least prevention being found in plants tested one week after pre-inoculation. The results demonstrate that introduction of a non-estrogenic CMV satellite via pre-inoculation, or "vaccination", into tomato plants will prevent severe disease following later infection by a severe strain of CMV. The pre-inoculation method has the advantage of providing a rapid response to viral epidemics and the satellite mediated protection of tomato and pepper against CMV infection has been tested. As noted above, this method is effective against fungal diseases, as well as PSTV.

It is to be understood that the present invention is not limited to the embodiment described above, but encompasses any and all embodiments within the scope of the following claims.

I claim:

1. A biological control agent for plants, comprising an isolated strain of cucumber mosaic virus having an associated satellite RNA of SEQ ID NO: 1.

2. A method of protecting plants from disease, comprising the step of inoculating an uninfected plant with a therapeutically effective dose of a strain of cucumber mosaic virus having an associated satellite RNA of SEQ ID NO: 1; and subjecting said plants to a disease causing agent.

3. The method of protecting plants from disease according to claim 2, wherein the disease is caused by a strain of cucumber mosaic virus having an associated satellite RNA of SEQ ID NO: 2.

4. The method of protecting plants from disease according to claim 2, wherein the disease causing agent comprises potato spindle tuber viroid (PSTV).

5. The method of protecting plants from disease according to claim 2, wherein the disease causing agent comprises *fusarium* wilt.

6. The method of protecting plants from disease according to claim 2, wherein the disease causing agent comprises leaf-spotting disease.

7. The method of protecting plants from disease according to claim 2, wherein said step of inoculating comprises the steps of:

grinding the tissues of plants infected with cucumber mosaic virus having an associated satellite RNA of SEQ ID NO: 1 in a 0.01 M potassium phosphate buffer (pH 7.1); and rubbing the leaves with the ground CMV-infected tissues over the leaves of the healthy plant with a cotton swab.

8. The method of protecting plants from disease according to claim 2, wherein said step of inoculating comprises the steps of:

extracting total nucleic acids from the tissues of plants infected with cucumber mosaic virus having an associated satellite RNA of SEQ ID NO: 1 into an extraction solvent;

precipitating the total nucleic acids from the extraction solvent;

dissolving the precipitated total nucleic acids in distilled water to form a suspension; and inoculating the leaves of the healthy plant with the suspension using a gloved finger.

9. A method of protecting plants from disease, comprising the step of inoculating an uninfected plant with a therapeutically effective dose of a strain of cucumber mosaic virus having an associated satellite RNA of SEQ ID NO: 1.

* * * * *